(12) United States Patent
Todd

(10) Patent No.: US 11,090,260 B2
(45) Date of Patent: Aug. 17, 2021

(54) SINGLE-DOSE DUAL-COMPARTMENT DRUG DELIVERY SYSTEM

(71) Applicant: CELLULA LLC, Villanova, PA (US)

(72) Inventor: Damian Joseph Todd, Villanova, PA (US)

(73) Assignee: CELLULA LLC, Villanova, PA (US)

( * ) Notice: Subject to any disclaimer, the term of this patent is extended or adjusted under 35 U.S.C. 154(b) by 53 days.

(21) Appl. No.: 16/274,163

(22) Filed: Feb. 12, 2019

(65) Prior Publication Data

US 2019/0247298 A1    Aug. 15, 2019

Related U.S. Application Data

(60) Provisional application No. 62/629,624, filed on Feb. 12, 2018.

(51) Int. Cl.
*B65D 25/08*    (2006.01)
*A61K 9/00*    (2006.01)
(Continued)

(52) U.S. Cl.
CPC .......... *A61K 9/0014* (2013.01); *A61F 9/0008* (2013.01); *A61J 1/2093* (2013.01); *B65D 25/08* (2013.01); *B65D 81/3266* (2013.01); *A61K 9/0043* (2013.01); *A61K 9/0046* (2013.01); *A61K 9/0048* (2013.01);
(Continued)

(58) Field of Classification Search
CPC .. A61K 9/0014; A61K 9/0043; A61K 9/0048; A61K 9/0046; A61K 9/0075; A61K 2800/882; A61F 9/0008; A61M 15/0035; B65D 81/3266; B65D 25/08; B65D 81/32;
(Continued)

(56) References Cited

U.S. PATENT DOCUMENTS 3,128,920 A * 4/1964 Volckening et al. .. B65D 75/48
222/215
3,429,429 A * 2/1969 Poitras ............... B65D 81/3272
206/222
(Continued)

FOREIGN PATENT DOCUMENTS

CN    1138462    * 12/1996    ............. A61K 35/51

OTHER PUBLICATIONS

English Translation of CN 1138462 (Year: 1996).*

*Primary Examiner* — Steven A. Reynolds
(74) *Attorney, Agent, or Firm* — Volpe Koenig

(57) ABSTRACT

A single use applicator described herein allows for simplicity while ensuring that only the necessary amount of product in each compartment is utilized when needed. The inventive drug delivery device includes a housing with two compartments, each containing substances separated by a barrier or membrane which can be broken apart by applying pressure to the housing. One end of the applicator includes a tapered nozzle and cap which can be twisted off when ready to use. Once the barrier or membrane is broken, the two components, liquid and powder, will mix creating the end product. After the two components have been mixed and the user is ready to apply the end product, the user will twist the cap off of the device and apply pressure to the applicator housing in order to force the substance through the nozzle and into the eye, nasal passage, ear canal or other part of the body.

6 Claims, 1 Drawing Sheet

(51) Int. Cl.
*A61F 9/00* (2006.01)
*B65D 81/32* (2006.01)
*A61J 1/20* (2006.01)
*A61M 15/00* (2006.01)

(52) U.S. Cl.
CPC ...... *A61K 9/0075* (2013.01); *A61K 2800/882* (2013.01); *A61M 15/0035* (2014.02)

(58) Field of Classification Search
CPC . B65D 81/3211; B65D 81/3261; A61J 1/2093
USPC .......................................................... 206/219
See application file for complete search history.

(56) References Cited

U.S. PATENT DOCUMENTS

| | | | |
|---|---|---|---|
| 3,917,120 A * | 11/1975 | Larenz | B65D 75/48 222/129 |
| 3,993,223 A * | 11/1976 | Welker, III | B65D 1/095 222/107 |
| 4,871,091 A * | 10/1989 | Preziosi | A61F 9/0008 222/92 |
| 5,287,961 A * | 2/1994 | Herran | B65D 81/3266 206/219 |
| 5,320,845 A | 6/1994 | Py | |
| 5,425,475 A * | 6/1995 | Clark | B65D 35/28 222/103 |
| 5,425,480 A * | 6/1995 | Rabenau | A61F 9/0008 206/229 |
| 5,875,931 A | 3/1999 | Py | |
| 5,997,518 A | 12/1999 | Laibovitz et al. | |
| 6,007,264 A * | 12/1999 | Koptis | B32B 3/02 401/132 |
| 6,179,819 B1 * | 1/2001 | Haswell | A61M 1/0236 128/854 |
| 6,241,124 B1 * | 6/2001 | Hoyt | A61J 1/067 222/143 |
| 7,028,862 B2 * | 4/2006 | Poynter | A61J 1/00 222/209 |
| 2001/0047162 A1 * | 11/2001 | Yugari | A61M 5/282 604/410 |
| 2007/0253761 A1 | 11/2007 | May | |
| 2012/0123795 A1 * | 5/2012 | Brevnova | G06Q 10/083 705/2 |
| 2015/0203275 A1 * | 7/2015 | May | B05C 17/00583 206/219 |
| 2018/0050859 A1 * | 2/2018 | May | B65D 83/0005 |
| 2018/0319567 A1 * | 11/2018 | Miller | C04B 38/02 |
| 2020/0170998 A1 * | 6/2020 | Todd | A61K 9/0048 |

* cited by examiner

SINGLE-DOSE DUAL-COMPARTMENT DRUG DELIVERY SYSTEM

CROSS REFERENCE TO RELATED APPLICATION

This application claims the benefit of U.S. Provisional Application No. 62/629,624 filed Feb. 12, 2108, which is incorporated by reference as if fully set forth.

SUMMARY

The inventive single use applicator described herein allows for simplicity while ensuring that only the necessary amount of product in each compartment is utilized when needed. The inventive drug delivery device comprises a housing with two compartments, each containing substances separated by a barrier or membrane which can be broken apart by applying pressure to the housing. One end of the applicator comprises a tapered nozzle and cap which can be twisted off when ready to use. Once the barrier or membrane is broken, the two components, liquid and powder, will mix creating the end product. After the two components have been mixed and the user is ready to apply the end product, the user will twist the cap off of the device and apply pressure to the applicator housing in order to force the substance through the nozzle and into the eye, nasal passage, ear canal or other part of the body.

BRIEF DESCRIPTION OF THE DRAWINGS

A more detailed understanding may be had from the following description, given by way of example in conjunction with the accompanying drawings, wherein like reference numerals in the figures indicate like elements, and wherein.

DETAILED DESCRIPTION OF THE PREFERRED EMBODIMENTS

The embodiments disclosed herein relate to a system for delivering predetermined volumes of liquid preparations to the eye or other parts of the body. In one embodiment, the drug delivery system includes two separate compartments in a single use applicator, each of the two separate compartments being separated by a barrier or membrane which keeps the materials in the two compartments separate until pressure is applied to the system. Once pressure is applied to the system, for example, by way of squeezing the system, the barrier or membrane will break apart and the materials in the two compartments will mix, producing the final product to be applied from the system. This system, also referred to herein as an applicator, has application in performing treatments of the eye, ear, nose or other parts of a body in a single dosage and in a reliable manner. Current applicators do not have the ability to serve as a single dosage, disposable applicator that allows two separate ingredients to be mixed at the time of the users' choosing. Prior art delivery systems fail to provide a system for mixing a liquid component and a powder component, in the manner described above, for application at a time of the user's choosing. The inventive single-dose applicator may be disposable, and also allows for extended shelf life of the medication by keeping the unmixed ingredients in a sterile, unmixed state until ready for use.

The inventive single use applicator described herein allows for simplicity while ensuring that only the necessary amount of product in each compartment is utilized when needed. The inventive drug delivery device comprises a housing with two compartments, each containing substances separated by a barrier or membrane which can be broken apart by applying pressure to the housing. One end of the applicator comprises a tapered nozzle and cap which can be twisted off when ready to use. Once the barrier or membrane is broken, the two components, liquid and powder, will mix creating the end product. After the two components have been mixed and the user is ready to apply the end product, the user will twist the cap off of the device and apply pressure to the applicator housing in order to force the substance through the nozzle and into the eye, nasal passage, ear canal or other part of the body.

Figure 1:
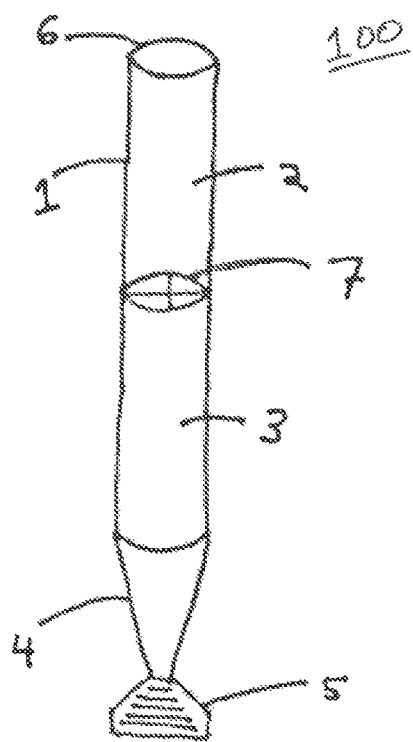
FIG. 1 is a diagram of the single-use, disposable applicator according to one embodiment of this disclosure.

Referring to FIG. 1, one embodiment of the disclosed applicator 100 is shown. While the applicator 100 is depicted as cylindrical in this embodiment, that is purely exemplary. Various shapes may be utilized for both ease of manufacturing and for surface area and mixing considerations of the components. The applicator 100 comprises a housing 1. In some embodiments, the housing 1 may be made from a firm plastic material or a rubber or resin material. Preferably, the housing 1 is constructed such that it is malleable enough that when pressure is applied by the fingers of a user of the applicator 100, a barrier 7 is ruptured or broken. This will be described in more detail below.

The housing 1 forms two compartments, the first compartment 2 and the second compartment 3. In one embodiment, the first compartment 2 contains a dry component, and the second compartment 3 contains a liquid component (although obviously this may be switched). The volume of these compartments may be changed based on the desired ratio of components to be mixed. Similarly, the shape of the housing 1 forming the first compartment 2 and second compartment 3 may be selected to increase or decrease the size of the interface between the first compartment 2 and second compartment 3. For example, the cylindrical shape of the housing 1 shown in FIG. 1 provides a relatively small interface, in terms of surface area, between the first compartment 2 and the second compartment 3. Instead of a cylinder, in another embodiment, the housing 1 is spherical, thus maximizing the surface area of the interface between a first compartment 2 and a second compartment 3. This size of this interface may be set as desired based on the solubility of the components to be mixed.

The housing 1 further comprises an applicator nozzle 4 and an applicator cap 5 on one end, and a base 6 at the other end. The applicator cap 5 and the base 6 may be affixed to the housing via screw threads, or they may be sealed plastic during manufacture. The applicator cap 5 and the base 6 serve to seal the applicator 100. During manufacture, components may be added to first compartment 2 and sealed by the base 6. Similarly, components may be added to the second compartment 3 and sealed by the applicator cap. The applicator nozzle 4 may be shaped to allow for proper application of the mixed solution. For example, the shape and opening of the applicator nozzle 4, once the applicator cap 5 has been removed, may produce a desired droplet size and/or shape. Additionally, the shape and contour of the applicator nozzle 4 may be selected to aid in the administration of the mixed solution, for example, depending on whether the mixed solution is to be applied to an eye, or to an ear, etc.

Still referring to FIG. 1, the first compartment 2 and the second compartment 3 of the applicator 100 are separated by barrier 7. Barrier 7 separates the components containing in the first compartment 2 and the second compartment 3. The barrier 7 is not permeable. However, barrier 7 is constructed such that when pressure is applied to the housing, for example by way of the user of the applicator 100 squeezing the housing 1 with their fingers, the pressure created by the first compartment 2 and/or the second compartment 3 ruptures the barrier 7 material 7. This rupture of the barrier 7 allows the contents of the first compartment 2 to mix with the contents of the second compartment 3. As mentioned above, in one embodiment, the dry component and liquid component mix after the barrier 7 has ruptured.

Figure 2:
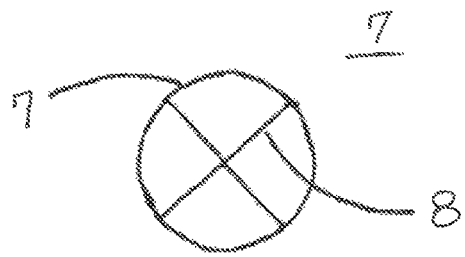
FIG. 2 is an illustration of the barrier shown in FIG. 1, according to one embodiment of this disclosure.

Referring now to FIG. 2, the barrier 7 is shown. It is important to note that the shape of the barrier 7 is exemplary. Since the applicator 100 described with reference to FIG. 1 is cylindrical, the barrier 7 is a cross section of the housing, and is therefore circular in shape. As mentioned above, the barrier 7 may be any shape selected for the specific components housed in the applicator 100. The barrier 7 may be constructed from the same material as the housing 1 described in FIG. 1, or it may be made of a different material. The barrier 7, in one embodiment, includes seams 8. The purpose of the seams 8 is to enable rupture of the barrier 7 when pressure is applied to the housing. Depending on the material of the barrier 7, the seams 8 may not be necessary. When the seams 8 are necessary, they may be arranged in a variety of ways selected such that the barrier 7 ruptures when the desired force is applied to the housing 1. FIG. 2 shows the seams 8 in an "X" arrangement, but this is exemplary.

In one embodiment, the applicator 100 is used as a single-use, disposable eye dropper to deliver umbilical cord blood derived serum to a patient's eye. This may be for the treatment of thermal and/or chemical burns or for the treatment of dry-eye syndrome. The umbilical cord blood is processed to extract the umbilical cord blood serum. The umbilical cord blood serum is then freeze dried, resulting in a powder. The freeze dried umbilical cord blood serum powder is placed in one compartment of the applicator 100. A sterile liquid solution is placed in the other compartment of the applicator 100. The sterile liquid solution may be sterile water, or it may be some other liquid solution. When pressure is applied to the housing 1 of the applicator 100, for example, by the user of the applicator 100 squeezing the applicator 100 between their fingers, the barrier 7 ruptures, permitting mixing of the freeze dried umbilical cord blood serum in one compartment and the sterile liquid solution in the other compartment. The user of the applicator 100 may then shake the solution as necessary to encourage mixing of the components. The applicator cap 5 can then be removed by the user, and the reconstituted umbilical cord blood serum may be applied to the user's eye in a typical eye dropper fashion.

What is claimed is:

1. A single-use, disposable applicator for treating dry-eye syndrome, the applicator comprising:
   a housing comprising a first compartment and a second compartment;
      the first compartment contains freeze dried human umbilical cord blood serum, and
      the second compartment contains a liquid configured to reconstitute the freeze dried human umbilical cord blood serum upon mixing;
   a barrier positioned inside the housing between the first compartment and the second compartment,
      in a first state, the barrier seals the first compartment from the second compartment,
      in a second state, upon application of a first pressure to the housing, the barrier is configured to rupture and allow mixing of the freeze dried human umbilical cord blood serum in the first compartment with the liquid in the second compartment to create reconstituted human umbilical cord blood serum; and
   an applicator nozzle configured to dispense drops of the reconstituted human umbilical cord blood serum when a second pressure is applied to the housing.

2. The single-use, disposable applicator of claim 1, wherein the first pressure is a first predetermined pressure.

3. The single-use, disposable applicator of claim 1, wherein the second pressure is a second predetermined pressure.

4. The single-use, disposable applicator of claim 1, wherein the barrier is the same material as the housing.

5. The single-use, disposable applicator of claim 1, wherein a thickness of the barrier material is less than a thickness of the housing material.

6. The single-use, disposable applicator of claim 1, wherein the housing is cylindrical.

* * * * *